(12) United States Patent
Eckard et al.

(10) Patent No.: US 11,382,291 B2
(45) Date of Patent: Jul. 12, 2022

(54) CORN PLANTS WITH IMPROVED DISEASE RESISTANCE

(71) Applicant: SEMINIS VEGETABLE SEEDS, INC., St. Louis, MO (US)

(72) Inventors: Jonathan Tyler Eckard, Richmond, CA (US); David Elon Fisher, Waunakee, WI (US); Tim J. Gustafson, Sun Prairie, WI (US)

(73) Assignee: SEMINIS VEGETABLE SEEDS, INC, St. Louis, MO (US)

( * ) Notice: Subject to any disclaimer, the term of this patent is extended or adjusted under 35 U.S.C. 154(b) by 129 days.

(21) Appl. No.: 16/721,159

(22) Filed: Dec. 19, 2019

(65) Prior Publication Data

US 2020/0199610 A1     Jun. 25, 2020

Related U.S. Application Data

(60) Provisional application No. 62/783,899, filed on Dec. 21, 2018.

(51) Int. Cl.
| | |
|---|---|
| *A01H 6/46* | (2018.01) |
| *A01H 1/00* | (2006.01) |
| *C12N 15/82* | (2006.01) |
| *A01H 5/10* | (2018.01) |

(52) U.S. Cl.
CPC ............. *A01H 1/1255* (2021.01); *A01H 5/10* (2013.01); *A01H 6/4684* (2018.05); *C12N 15/8261* (2013.01)

(58) Field of Classification Search
CPC .................................................. A01H 1/1255
See application file for complete search history.

(56) References Cited

U.S. PATENT DOCUMENTS

| | | |
|---|---|---|
| 2012/0017338 A1 | 1/2012 | Wu et al. |
| 2015/0240253 A1 | 8/2015 | McGonigle et al. |
| 2016/0201080 A1* | 7/2016 | Ouzunova ............ C07K 14/415 800/279 |
| 2017/0172098 A1 | 6/2017 | Bourdoncle et al. |
| 2019/0119698 A1 | 4/2019 | Brugmans et al. |

OTHER PUBLICATIONS

Robbins, William Alonzo, Jr. PhD Dissertation Purdue University The Inheritance of a New Source of Resistance To Exserohilum Turcicum (Pass) Leonard and Suggs Derived From the Maize (*Zea mays* L.) Variety 'Mayorbella' (PI 209135) (Year: 1983).*
Levy et al. Phytoparasitica vol. 20, No. 1, pp. 53-66 (Year: 1992).*
Warren Crop Science vol. 21, No. 3, p. 477 (Year: 1981).*
Warren, H.L., "Registration of H110 and H111 Maize Germplasm," Crop Sci., 1982, 1270-1271, 22(6).
PI 550527, U.S. National Plant Germplasm System, npgsweb.ars-grin.gov/gringlobal/accessiondetail.aspx? id=1445463. Accessed on Feb. 11, 2020.
International Search Report and Written Opinion regarding International Application No. PCT/2019/067384, dated May 5, 2020.
GenBank Accession No. KR014666, dated Jul. 16, 2015.
Invitation to Pay Additional Fees regarding International Application No. PCT/2019/067384, dated Mar. 9, 2020.
Welz et al., "QTLs for resistance to Setosphaeria turcica in an early maturing DentXFlint maize population", Theor Appl Genet (1999) 99(3-4):649-655.

* cited by examiner

*Primary Examiner* — David H Kruse
(74) *Attorney, Agent, or Firm* — Dentons US LLP; Alissa Eagle (57) ABSTRACT

Corn plants exhibiting broad-spectrum resistance to *Exserohilum turcicum* are provided, together with methods of producing, identifying, or selecting plants or germplasm with a *Exserohilum turcicum* resistance phenotype. Such plants include sweet corn plants as well as agronomically elite dent corn plants comprising introgressed genomic regions conferring disease resistance. Compositions, including novel polymorphic markers and methods for producing, breeding, identifying, and selecting plants or germplasm with a disease resistance phenotype are further provided.

20 Claims, 4 Drawing Sheets

Specification includes a Sequence Listing.

FIG. 1

| NLB race | Ht1 | Ht2 | HtN | HtX |
|---|---|---|---|---|
| Race 0 | R | R | R | R |
| Race 1 | S | R | R | R |
| Race 2 | R | S | R | R |
| Race 12 | S | S | R | R |
| Race 1N | S | R | S | R |
| Race 2N | R | S | S | R |

FIG. 2

| NLB race \ Market region | NAM | EMEA | SAM |
|---|---|---|---|
| Race 0 | 0.23 | 0.41 | 0.68 |
| Race 1 | 0.62 (0.50) | 0.33 | 0.06 |
| Race 2 | 0.09 | 0.14 | 0.13 |
| Race 12 | 0.01 | 0.02 | 0.00 |
| Race N/1N | 0.01 (0.13) | 0.01 | 0.13 |
| Race 2N | 0.04 | 0.09 | 0.00 |
| Survey year | 2004 (2016) | 2012 | 2015 |

CORN PLANTS WITH IMPROVED DISEASE RESISTANCE

CROSS-REFERENCE TO RELATED APPLICATIONS

This application claims the benefit of priority of U.S. Provisional Appl. Ser. No. 62/783,899, filed Dec. 21, 2018, the disclosure of which is hereby incorporated by reference in its entirety.

INCORPORATION OF SEQUENCE LISTING

A sequence listing containing the file named "SEMB040US_ST25.txt" which is 4 kilobytes (measured in MS-Windows®) and created on Dec. 17, 2019, and comprises 5 sequences, is incorporated herein by reference in its entirety.

FIELD OF THE INVENTION

The present invention relates to the field of plant breeding and more specifically to methods and compositions for producing corn plants exhibiting improved disease resistance.

BACKGROUND

Disease resistance is an important trait in agriculture, particularly for the production of food crops. Although disease resistance alleles have been identified in maize plants, efforts to combine several disease resistance traits in a single plant line have been hindered by tightly linked or even allelic loci conferring resistance to different pathogens. Introducing disease resistance is further complicated by high densities of repeated sequences in regions of plant genomes controlling disease resistance, which can greatly reduce the possibility of developing useful genetic markers. The identification of additional genes that confer resistance to multiple races of pathogens is desired.

SUMMARY

The present invention provides an agronomically elite corn plant comprising an introgression from *Zea mays* var. *indentata* on chromosome 8, wherein said introgression comprises a single gene conferring broad-spectrum resistance to *Exserohilum turcicum* relative to a plant lacking said introgression, and wherein said resistance is additive. In certain embodiments, the introgression comprises a chromosomal segment from *Zea mays* var. *indentata* at marker M1 (SEQ ID NO: 1) in said plant. In further embodiments, the introgression is about 12 cM or less in size. In yet other embodiments, the plant is homozygous for the introgression. In additional embodiments, a sample of seed comprising the introgression was deposited under ATCC Accession Number PTA-125393.

In certain aspects, the broad-spectrum resistance comprises resistance to a plurality of *Exserohilum turcicum* races. For example, the broad-spectrum resistance comprises resistance to *Exserohilum turcicum* races 1, 2, M, and N.

The present invention additionally provides a plant part of a corn plant comprising an introgression from *Zea mays* var. *indentata* on chromosome 8, wherein said introgression comprises a single gene conferring broad-spectrum resistance to *Exserohilum turcicum* relative to a plant lacking said introgression, and wherein said resistance is additive. In certain embodiments, the plant part is a cell, a seed, a root, a stem, a leaf, an ear, a flower, or pollen.

In addition, the present invention provides an introgression fragment comprising a recombinant chromosomal segment from *Zea mays* var. *indentata* at marker locus M1 (SEQ ID NO: 1). In certain embodiments, the fragment confers broad-spectrum resistance to *Exserohilum turcicum*. In other embodiments, a sample of seed comprising said introgression was deposited under ATCC Accession Number PTA-125393.

The present invention also provides a method for producing a plant of an agronomically elite corn variety with improved resistance to *Exserohilum turcicum*, comprising introgressing into said plant a chromosomal segment from *Zea mays* var. *indentata* on chromosome 8 that confers broad-spectrum resistance to *Exserohilum turcicum* relative to a plant lacking said introgression, and wherein said resistance is additive. In some embodiments, the broad-spectrum resistance comprises resistance to a plurality of *Exserohilum turcicum* races. In further embodiments, the broad-spectrum resistance comprises resistance to *Exserohilum turcicum* races 1, 2, M, and N. In yet further embodiments, a sample of seed comprising said chromosomal segment was deposited under ATCC Accession Number PTA-125393. In some embodiments, the introgressing comprises backcrossing. In other embodiments, the introgressing comprises marker-assisted selection. In certain embodiments, the introgressing comprises assaying for said broad-spectrum resistance to *Exserohilum turcicum*. In some embodiments, the introgressing comprises crossing a plant comprising said chromosomal segment with itself or with a second corn plant of a different genotype to produce one or more progeny plants and selecting a progeny plant comprising said chromosomal segment. In particular embodiments, selecting a progeny plant comprises detecting a nucleic acid comprising marker locus M1 (SEQ ID NO: 1). In further embodiments, the progeny plant is an $F_2$-$F_6$ progeny plant. In selected embodiments, producing the progeny plant comprises backcrossing. The present invention further provides corn plants obtainable by the methods provided herein.

In addition, the present invention provides a method for selecting an agronomically elite corn plant with improved resistance to *Exserohilum turcicum*, comprising crossing a corn plant comprising an introgression from *Zea mays* var. *indentata* on chromosome 8, wherein said introgression comprises a single gene conferring broad-spectrum resistance to *Exserohilum turcicum* relative to a plant lacking said introgression, and wherein said resistance is additive with itself or with a second corn plant of a different genotype to produce one or more progeny plants, and selecting a progeny plant comprising said introgression. In some embodiments, selecting said progeny plant comprises detecting a marker locus genetically linked to said introgression. In certain embodiments, selecting said progeny plant comprises detecting a nucleic acid comprising marker locus M1 (SEQ ID NO: 1). In other embodiments, said resistance comprises resistance to a plurality of *Exserohilum turcicum* races. In further embodiments, said resistance comprises resistance to *Exserohilum turcicum* races 1, 2, M, and N. In some embodiments, said progeny plant is an $F_2$-$F_6$ progeny plant. In other embodiments, producing said progeny plant comprises backcrossing.

In addition, the present invention provides an agronomically elite corn plant comprising an introgression from *Zea mays* var. *indentata* on chromosome 8, wherein said introgression comprises a single gene conferring broad-spectrum resistance to *Exserohilum turcicum* relative to a plant lacking said introgression, wherein said plant further comprises a recombinant chromosomal segment that comprises a first allele comprising an Ht2 locus and a second allele comprising an HtN locus, wherein said first allele and said second allele are configured in cis linkage on chromosome 8, and wherein said recombinant chromosomal segment confers resistance to *Exserohilum turcicum*. In some embodiments, the recombinant chromosomal segment is flanked by marker loci Q-NZMAY009401770 (SEQ ID NO: 2) and Q-NZ-MAY009430172 (SEQ ID NO: 5) on chromosome 8. In other embodiments, the recombinant chromosomal segment is flanked by marker loci Q-ZMHt2 (SEQ ID NO: 3) and Q-NZMAY009238970 (SEQ ID NO: 4) on chromosome 8.

In addition, the present invention provides an agronomically elite dent corn plant comprising an introgression from *Zea mays* var. *indentata* on chromosome 8, wherein said introgression comprises a single gene conferring broad-spectrum resistance to *Exserohilum turcicum* relative to a plant lacking said introgression. In some embodiments, the introgression comprises a chromosomal segment from *Zea mays* var. *indentata* at marker M1 (SEQ ID NO: 1) in said plant. In other embodiments, the broad-spectrum resistance comprises resistance to a plurality of *Exserohilum turcicum* races. In some embodiments, the plant is homozygous for said introgression. In other embodiments, a sample of seed comprising said introgression was deposited under ATCC Accession Number PTA-125393.

In addition, the present invention provides a method for producing a plant of an elite corn variety with improved resistance to *Exserohilum turcicum*, comprising introgressing into an elite corn variety a chromosomal segment from *Zea mays* var. *indentata* on chromosome 8 that confers broad-spectrum resistance to *Exserohilum turcicum* relative to a plant lacking said introgression, and wherein said resistance is additive. In some embodiments, said introgressing comprises crossing a plant comprising said chromosomal segment with itself or with a second corn plant of a different genotype to produce one or more progeny plants; and selecting a progeny plant comprising said chromosomal segment. In some embodiments, said selecting a progeny plant comprises detecting a nucleic acid comprising marker locus M1 (SEQ ID NO: 1). In other embodiments, the elite corn variety is a dent, flint or sweet corn variety. In some embodiments, the progeny plant is an $F_2$-$F_6$ progeny plant. The present invention further provides corn plants obtainable by the methods provided herein.

DETAILED DESCRIPTION

Northern Leaf Blight (NLB) is caused by the ascomycete *Exserohilum turcicum*, which is also known as *Setosphaeria turcica*, and results in a significant reduction in yield and quality in maize (*Zea mays* L.) crops. *Exserohilum turcicum* overwinters as dormant mycelium or as chlamydospores in the soil in host plant debris and infects new maize plants by airborne conidia spores. Depending on the host, pathogen, and environmental conditions, the first symptoms typically appear fourteen days after infection and grow to 2-30 cm long elliptical lesions of gray-green color, which turn tan brown parallel to leaf margins. In bad years or when no host resistance is available, the infection can spread through the whole leaf, leading to blighting of the entire leaf. Infections are favored under humid conditions and moderate temperatures. This, together with the fact that the fungal lesions grow faster at night, makes it an especially devastating disease of maize in tropical and subtropical regions. However, NLB is also present in maize in temperate regions. The effects of NLB can be diminished by fungicides, biological control, and improved management practices. The effectiveness of these methods can be increased if, the plant is resistant to *Exserohilum turcicum* as well.

Figure 1:
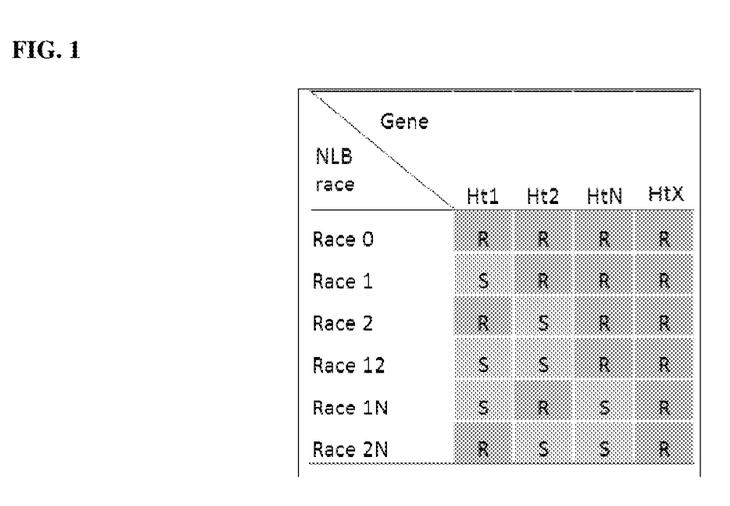
FIG. 1: Shows a compatibility profile between *Exserohilum turcicum* races and Ht genes. An "S" indicates that the gene and race are compatible and thus plants with this gene are susceptible to that race and an "R" indicates that the gene and race are incompatible and thus plants with this gene are resistant to that race.
Figure 2:
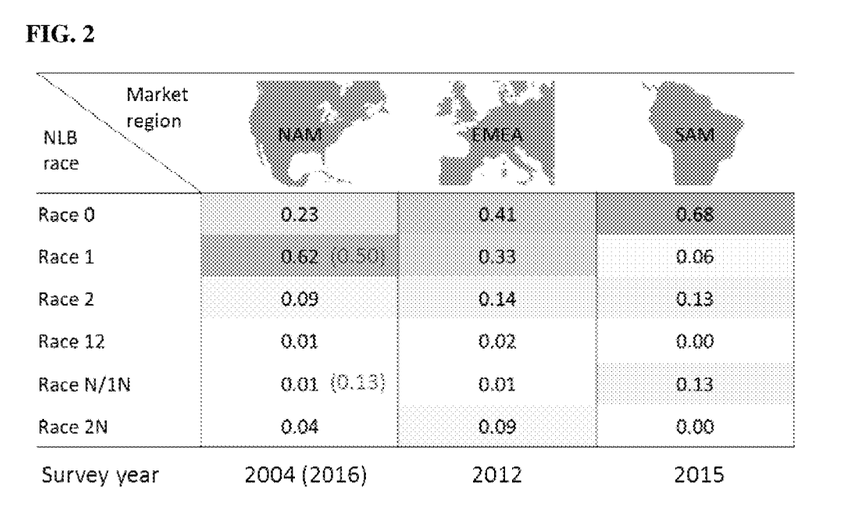
FIG. 2: Shows a chart displaying the distribution of *Exserohilum turcicum* races in key sweet corn market regions.

Resistance to NLB caused by *Exserohilum turcicum* comes in two forms: quantitative resistance, which consists of multiple loci that each contribute a small amount to the resistance level of the plant, or qualitative resistance, which consists single, race specific genes which provide high levels of resistance. While qualitative resistance is often absolute resistance, to date, the qualitative resistance against NLB in maize has not been absolute and typically provides resistance which delays the onset of *Exserohilum turcicum* infection past the plant life stages where infection would most affect yield and quality. Under environmental conditions beneficial for the growth of *Exserohilum turcicum*, the disease pressure can become severe enough to overcome the qualitative resistance. Qualitative resistance is based on an interaction between the Ht genes of the plant and the Avirulence (avr) gene of the fungus (FIG. 1). When these interactions are incompatible, *Exserohilum turcicum* cannot infect the plant. To date, nine different Ht genes from different sources have been identified: Ht1 on chromosome 2, Ht2, HtNB, and Htn1 on chromosome 8, Ht3 on chromosome 7, ht4 on chromosome 1, HtM whose location is unknown, HtP on chromosome 2, and rt on chromosome 3. The naming of the genes is directly linked to the naming of the races of *Exserohilum turcicum*. Each *Exserohilum turcicum* race is designated according to the compatible Ht gene, i.e. the race can infect plants with the relevant gene. For example, *Exserohilum turcicum* race 12 can infect plants with the Ht1 and/or Ht2 genes. Genes HtNB and Htn1, which are both known as and collectively referred to herein as HtN, are derived from different sources but both are compatible with *Exserohilum turcicum* races containing the avr gene and have the same resistance profile. Qualitative resistance is not necessarily durable as the appearance of a compatible *Exserohilum turcicum* race can render the Ht gene ineffective. Furthermore, *Exserohilum turcicum* populations generally consist of mixtures of different races. The composition of races varies by geographic region (FIG. 2).

Therefore, breeders generally have tried to combine different Ht genes to produce resistance cultivars. However, this is not always easy or possible as the Ht genes are derived from different sources and/or species, and the sources have diverse genetic backgrounds. In addition, if genes are located in a similar region on the genome (such as Ht2 and HtN) it is difficult to combine the genes in a cis-configuration. It is even more difficult to introduce quantitative resistance in a breeding population as the small resistance effects of individual loci are difficult to detect and a breeder must ensure all resistance genes are transferred in order to obtain the resistance level of the donor plant. The identification and ability to use a single gene that confers resistance to all prevalent Exserohilum turcicum races would simplify breeding significantly and would provide significant benefits.

The inventors have identified a novel Ht gene in maize that confers broad-spectrum resistance to more than one race of Exserohilum turcicum. In specific embodiments, the gene provides resistance to any combination of at least two races of Exserohilum turcicum selected from the group of race 1, race 2, race N, and race M. HtX is in the same gene cluster on chromosome 8 as Ht2 and HtN. The resistance provided by the HtX gene is additive. A homozygous configuration of HtX will confer a higher level of resistance. The HtX resistance gene was identified in maize line H111, developed by the Agricultural Experiment Station of Purdue University and the USDA, ARS. As explained in Example 4, approximately 50% of the H111 genome is derived from dent line B37 and the other approximately 50% from the open-pollinated population PI 209135. PI 209135 is also known as Mayorbela and is of tropical origin. Given the heterogeneous nature of PI 209135, a number of other genetically distinct lines have been derived from this population.

The present inventors have discovered for the first time that M1, a trait-linked SNP marker with a [C/T] change at 157,566,509 bp on chromosome 8 of the public maize B73 reference genome version 4.0 (B73 RefGen_v4), can be used to track and introgress the HtX gene into elite germplasm, and to distinguish it from the resistance conferred by Ht2 and HtN even though these genes are located in the same genomic region. The public reference genome of maize is available at, for example, the Maize Genetics and Genomics Database at maizegdb.org, and one skilled in the art would understand that the marker sequence provided for the first time in the instant application could be located on any version (including later versions) of the public genome. One aspect of the invention therefore provides sweet corn and agronomically elite corn plants comprising an introgression, wherein the introgression comprises a chromosomal segment from Zea mays var. indentata at marker M1 (SEQ ID NO: 1).

In certain embodiments, corn plants are provided comprising an introgression from Zea mays var. indentata on chromosome 8, wherein said introgression comprises a single gene conferring broad-spectrum resistance to Exserohilum turcicum relative to a plant lacking said introgression. In further embodiments, the broad-spectrum resistance to Exserohilum turcicum is additive.

In other embodiments, the invention provides plants comprising one or more of the novel recombinant introgressions provided herein. These novel introgressions provide robust broad-spectrum resistance to Exserohilum turcicum. In some embodiments, broad-spectrum resistance comprises resistance to a plurality of Exserohilum turcicum races. In further embodiments, the broad-spectrum resistance comprises resistance to Exserohilum turcicum races 1, 2, M, and N. Methods of producing the plants described herein are further provided.

The invention further provides novel trait-linked markers which can be used to produce corn plants comprising novel introgressions on chromosome 8 conferring broad-spectrum resistance to Exserohilum turcicum as described herein. In particular embodiments, the invention provides the trait-linked marker M1 (SEQ ID NO: 1).

Methods of producing plants comprising the chromosomal segment from Zea mays var. indentata described herein are further provided. In some examples, donor DNA from a resistant donor parent is introgressed into a corn line (the recurrent parent line). M1 (SEQ ID NO: 1) is used to select the allele of the resistance donor parent.

In certain embodiments, the invention provides methods of producing or selecting a corn plant exhibiting improved resistance to Exserohilum turcicum comprising: a) crossing a corn plant provided herein with itself or with a second corn plant of a different genotype to produce one or more progeny plants; and b) selecting a progeny plant comprising said introgression. In some embodiments, methods of the invention comprise selecting a progeny plant by detecting a nucleic acid comprising marker locus M1 (SEQ ID NO: 1).

Because genetically diverse plant lines can be difficult to cross, the introgression of Exserohilum turcicum resistance alleles into cultivated lines using conventional breeding methods could require prohibitively large segregating populations for progeny screens with an uncertain outcome. Marker-assisted selection (MAS) is therefore essential for the effective introgression of Exserohilum turcicum resistance alleles into elite cultivars. This has been complicated by the previous inability to resolve the specific regions associated with disease resistance. For the first time, the present invention enables effective MAS by providing improved and validated markers for detecting genotypes associated with disease resistance without the need to grow large populations of plants to maturity in order to observe the phenotype.

I. Genomic Regions, Alleles, and Polymorphisms Associated with Disease Resistance in Corn Plants Northern Leaf Blight (NLB) is a foliar disease caused by Exserohilum turcicum, also known as Setosphaeria turcica, which causes significant yield losses in maize crops. Exserohilum turcicum resistance loci have been identified, including Ht1, Ht2, Ht3, HtN, and HtM. Both Ht2 and HtN reside in a Exserohilum turcicum resistance gene cluster on chromosome 8 (NLB_8.1), while Ht1 resides on chromosome 2. Each of these genes confers resistance to certain Exserohilum turcicum isolates. In order to produce a maize plant with broad spectrum and durable resistance to Exserohilum turcicum, several different resistance loci and alleles may be combined in a single maize line. By combining the different loci the plant will have broad spectrum and durable resistance. The resistance is likely to be durable as it is unlikely that the pathogens will evolve to overcome the multiple modes of resistance. The invention provides novel introgressions of one or more alleles associated with broad-spectrum resistance to Exserohilum turcicum in corn plants, together with polymorphic nucleic acids and linked markers for tracking the introgressions during plant breeding.

Maize lines exhibiting Exserohilum turcicum resistance are known in the art and may be used together with the novel trait-linked markers provided herein in accordance with certain embodiments of the invention. For example, line H111, which also carries the designation PI 550527, can be used as a source for *Exserohilum turcicum* resistance. This source is available at the U.S. National Plant Germplasm System and the North Central Plant Introduction Station in Ames, Iowa, USA. In addition, the seed deposited under ATCC Accession No. PTA-125393 may be used as a source for the resistance trait.

Using the improved genetic markers and assays of the invention, the present inventors were able to successfully identify a novel introgression from *Zea mays* var. *indentata* that confers broad-spectrum resistance to *Exserohilum turcicum* in a plant. In certain embodiments, the invention provides sweet corn plants comprising *Zea mays* var. *indentata* DNA at marker locus M1 (SEQ ID NO: 1) on chromosome 8. In other embodiments, the invention provides agronomically elite corn plants of any type comprising this marker locus and the broad-spectrum resistance to *Exserohilum turcicum* associated therewith.

The novel introgressions provided herein confer board-spectrum resistance to *Exserohilum turcicum*, without the need to combine multiple race-specific resistance loci. The invention therefore represents a significant advance in the art.

II. Introgression of Genomic Regions Associated with *Exserohilum turcicum* Resistance Marker-assisted introgression involves the transfer of a chromosomal region defined by one or more markers from a first genetic background to a second. Offspring of a cross that contain the introgressed genomic region can be identified by the combination of markers characteristic of the desired introgressed genomic region from a first genetic background and both linked and unlinked markers characteristic of the second genetic background.

The present invention provides novel accurate markers for identifying and tracking introgression of one or more of the genomic regions disclosed herein from a *Exserohilum turcicum* resistant plant into a sweet corn line. The invention further provides markers for identifying and tracking the novel introgressions disclosed herein during plant breeding, including the marker M1.

Markers within or linked to any of the genomic intervals of the present invention may be useful in a variety of breeding efforts that include introgression of genomic regions associated with disease resistance into a desired genetic background. For example, a marker within 40 cM, 20 cM, 15 cM, 10 cM, 5 cM, 2 cM, or 1 cM of a marker associated with disease resistance described herein can be used for marker-assisted introgression of genomic regions associated with a disease resistant phenotype.

Maize plants comprising one or more introgressed regions associated with a desired phenotype wherein at least 10%, 25%, 50%, 75%, 90%, or 99% of the remaining genomic sequences carry markers characteristic of the recurrent parent germplasm are also provided. Sweet corn plants comprising an introgressed region comprising regions closely linked to or adjacent to the genomic regions and markers provided herein and associated with a disease resistance phenotype are also provided.

III. Development of Disease Resistant Maize Varieties

For most breeding objectives, commercial breeders work with germplasm that is "cultivated," "cultivated type," or "elite." As used herein, "elite" or "cultivated" variety means a variety that has resulted from breeding and selection for superior agronomic performance for use in agriculture. This includes the parents of a hybrid variety that may be cultivated, as well the variety that is itself cultivated. These cultivated lines may be used as recurrent parents or as a source of recurrent parent alleles during breeding. Cultivated or elite germplasm is easier to breed because it generally performs well when evaluated for horticultural performance. Many cultivated sweet corn types have been developed and are known in the art as being agronomically elite and appropriate for commercial cultivation. However, the performance advantage a cultivated germplasm provides can be offset by a lack of allelic diversity. Breeders generally accept this tradeoff because progress is faster when working with cultivated material than when breeding with genetically diverse sources.

In contrast, when cultivated germplasm is crossed with non-cultivated germplasm, a breeder can gain access to novel alleles from the non-cultivated type. Non-cultivated germplasm may be used as a source of donor alleles during breeding. However, this approach generally presents significant difficulties due to fertility problems associated with crosses between diverse lines, and negative linkage drag from the non-cultivated parent. In maize plants, non-cultivated plant types can provide alleles associated with disease resistance. However, these non-cultivated types may have poor horticultural qualities such as vulnerability to certain deleterious traits or diseases.

A maize or corn plant, as referenced herein, refers to any plant selected from the genus *Zea*, including, but not limited to, any plant selected from the species *Zea mays*. In further embodiments, the plant may be selected from the subspecies *Zea mays* L. ssp. *Mays*, for example *Zea mays* L. subsp. *mays Indentata*, otherwise known as dent corn; *Zea mays* L. subsp. *mays Indurata*, otherwise known as flint corn; *Zea mays* L. subsp. *mays Saccharata*, otherwise known as sweet corn; *Zea mays* L. subsp. *mays Amylacea*, otherwise known as flour corn; or *Zea mays* L. subsp. *mays Everta*, otherwise known as popcorn. *Zea* plants include hybrids, inbreds, partial inbreds, or members of defined or undefined populations.

The process of introgressing desirable resistance genes from non-cultivated lines into elite cultivated lines, while avoiding problems with linkage drag or low heritability, is a long and often arduous process. Success in deploying alleles derived from wild relatives therefore strongly depends on minimal or truncated introgressions that lack detrimental effects and reliable marker assays that replace phenotypic screens. Success is further defined by simplifying genetics for key attributes to allow focus on genetic gain for quantitative traits such as disease resistance. The process of introgressing genomic regions from non-cultivated lines can be greatly facilitated by the availability of accurate markers for marker-assisted selection (MAS).

One of skill in the art would therefore understand that the alleles, polymorphisms, and markers provided by the invention allow the tracking and introduction of any of the genomic regions identified herein into any genetic background. In addition, the genomic regions associated with disease resistance disclosed herein can be introgressed from one genotype to another and tracked using MAS. Thus, the Applicants" discovery of accurate markers associated with disease resistance will facilitate the development of maize plants having beneficial phenotypes. For example, seed can be genotyped using the markers of the present invention in order to select for plants comprising desired genomic regions associated with disease resistance, without the need for growing plants to maturity to evaluate phenotype. Moreover, MAS allows identification of plants homozygous or heterozygous for a desired introgression.

Inter-species crosses can also result in suppressed recombination and plants with low fertility or fecundity. For example, suppressed recombination has been observed for the tomato nematode resistance gene M1, the M1a and M1g genes in barley, the Yr17 and Lr20 genes in wheat, the Run1 gene in grapevine, and the Rma gene in peanut. Meiotic recombination is essential for classical breeding because it enables the transfer of favorable alleles across genetic backgrounds, the removal of deleterious genomic fragments, and pyramiding traits that are genetically tightly linked. Therefore suppressed recombination forces breeders to enlarge segregating populations for progeny screens in order to arrive at the desired genetic combination.

Phenotypic evaluation of large populations is time-consuming, resource-intensive and not reproducible in every environment. Marker-assisted selection offers a feasible alternative. Molecular assays designed to detect unique polymorphisms, such as SNPs, are versatile. However, they may fail to discriminate alleles within and among maize species in a single assay. Structural rearrangements of chromosomes such as deletions impair hybridization and extension of synthetically labeled oligonucleotides. In the case of duplication events, multiple copies are amplified in a single reaction without distinction. The development and validation of accurate and highly predictive markers are therefore essential for successful MAS breeding programs. A corn plant, seed, or cell provided herein can be genetically transformed.

Numerous methods for plant transformation have been developed, including biological and physical plant transformation protocols. See, for example, Miki et al., "Procedures for Introducing Foreign DNA into Plants" in *Methods in Plant Molecular Biology and Biotechnology*, Glick and Thompson Eds., CRC Press, Inc., Boca Raton, pp. 67-88 (1993). In addition, expression vectors and in vitro culture methods for plant cell or tissue transformation and regeneration of plants are available. See, for example, Gruber et al., "Vectors for Plant Transformation," in *Methods in Plant Molecular Biology and Biotechnology*, Glick and Thompson Eds., CRC Press, Inc., Boca Raton, pp. 89-119 (1993).

One method for introducing an expression vector into plants is based on the natural transformation system of *Agrobacterium*. See, for example, Horsch et al., A Simple and General Method for Transferring Genes into Plants. *Science*, 227:1229-1231 (1985). *A. tumefaciens* and *A. rhizogenes* are plant pathogenic soil bacteria which genetically transform plant cells. Descriptions of *Agrobacterium* vector systems and methods for *Agrobacterium*-mediated gene transfer are provided by, for example, U.S. Pat. No. 5,563,055, incorporated herein by reference in its entirety.

Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles. The expression vector is introduced into plant tissues with a biolistic device that accelerates the microprojectiles to speeds of 300 to 600 m/s which is sufficient to penetrate plant cell walls and membranes.

Another method for physical delivery of DNA to plants is sonication of target cells. Alternatively, liposome and spheroplast fusion have been used to introduce expression vectors into plants. Electroporation of protoplasts and whole cells and tissues can also be used.

Following transformation of corn target tissues, expression of the above-described selectable marker genes allows for preferential selection of transformed cells, tissues, and/or plants, using regeneration and selection methods well-known in the art.

The foregoing methods for transformation would typically be used for producing a transgenic variety. The transgenic variety could then be crossed with another (non-transformed or transformed) variety, in order to produce a new transgenic variety. Alternatively, a genetic trait which has been engineered into a particular corn line using the foregoing transformation techniques could be moved into another line using traditional backcrossing techniques that are well-known in the plant breeding arts. For example, a backcrossing approach could be used to move an engineered trait from a public, non-elite variety into an elite variety, or from a variety containing a foreign gene in its genome into a variety or varieties which do not contain that gene.

Many desirable traits, such as those described here, that can be introduced through introgression or transformation can also be introduced directly into a plant by the use of genome-editing molecular techniques. One aspect of the invention includes plants with a genome that has been changed by site-specific genome modification techniques.

A corn plant, seed, or cell provided herein can also be produced by one or more genome engineering techniques or subject to further genomic editing. For example, one or more NLB resistance alleles can be introduced into an NLB susceptible background. Exemplary genome engineering techniques include meganucleases, zinc-finger nucleases, TALENs, and CRISPR/Cas9 systems. See, e.g., Gaj et al., ZFN, TALEN, and CRISPR/Cas-based methods for genome engineering. *Trends in Biotechnology*, 31:397-405 (2013). Additional genome engineering techniques known to those of ordinary skill in the art are also envisioned. Techniques of site-specific genome modification include the use of enzymes such as, endonucleases, recombinases, transposases, helicases and any combination thereof. In one aspect, an endonuclease is selected from a meganuclease, a zinc-finger nuclease (ZFN), a transcription activator-like effector nuclease (TALEN), an Argonaute, and an RNA-guided nuclease, such as a CRISPR associated nuclease. In another aspect, the endonuclease is Cas9 or Cpf1.

Site-specific genome modification enzymes induce a genome modification such as a double-stranded DNA break (DSB) or single-strand DNA break at the target site of a genomic sequence that is then repaired by the natural processes of homologous recombination (HR) or non-homologous end-joining (NHEJ). Sequence modifications then occur at the cleaved sites, which can include deletions or insertions that result in gene disruption in the case of NHEJ, or integration of exogenous sequences by homologous recombination. These techniques, for example, may be used to alter another locus in a plant containing the coupling event of this invention, to alter the coupling event of this invention or to re-create the coupling event of this invention in a different plant background.

IV. Marker Assisted Breeding Techniques

Genetic markers that can be used in the practice of the present invention include, but are not limited to, restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (Indels), variable number tandem repeats (VNTRs), and random amplified polymorphic DNA (RAPD), isozymes, and other markers known to those skilled in the art. Marker discovery and development in crop plants provides the initial framework for applications to marker-assisted breeding activities (U.S. Patent Pub. Nos.: 2005/0204780, 2005/0216545, 2005/0218305, and 2006/0504538). The resulting "genetic map" is the representation of the relative position of characterized loci (polymorphic nucleic acid markers or any other locus for which alleles can be identified) to each other.

Polymorphisms comprising as little as a single nucleotide change can be assayed in a number of ways. For example, detection can be made by electrophoretic techniques including a single strand conformational polymorphism (Orita et al. (1989) *Genomics*, 8(2), 271-278), denaturing gradient gel electrophoresis (Myers (1985) *EPO* 0273085), or cleavage fragment length polymorphisms (Life Technologies, Inc., Gathersberg, Md.), but the widespread availability of DNA sequencing often makes it easier to simply sequence amplified products directly. Once the polymorphic sequence difference is known, rapid assays can be designed for progeny testing, typically involving some version of PCR amplification of specific alleles (PASA; Sommer, et al., *Biotechniques* 12(1), 82-87, 1992), or PCR amplification of multiple specific alleles (PAMSA; Dutton and Sommer, *Biotechniques*, 11(6), 700-7002, 1991).

Polymorphic markers serve as useful tools for assaying plants for determining the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a maize plant a genotype associated with disease resistance, identify a maize plant with a genotype associated with disease resistance, and to select a maize plant with a genotype associated with disease resistance. In certain embodiments of methods of the invention, polymorphic nucleic acids can be used to produce a maize plant that comprises in its genome an introgressed locus associated with disease resistance. In certain embodiments of the invention, polymorphic nucleic acids can be used to breed progeny maize plants comprising a locus associated with disease resistance.

Genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to different conditions of the allele at a locus.

Nucleic acid-based analyses for determining the presence or absence of the genetic polymorphism (i.e. for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with disease resistance in maize plants.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258,017; European Patent 237,362; European Patent 201, 184; U.S. Pat. Nos. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030, 787; 6,004,744; 6,013,431; 5,595,890; 5,762,876; 5,945, 283; 5,468,613; 6,090,558; 5,800,944; 5,616,464; 7,312, 039; 7,238,476; 7,297,485; 7,282,355; 7,270,981 and 7,250, 252 all of which are incorporated herein by reference in their entirety. However, the compositions and methods of the present invention can be used in conjunction with any polymorphism typing method to type polymorphisms in genomic DNA samples. These genomic DNA samples used include but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods, for example as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., *Genome Res.* 13:513-523, 2003); Cui et al., *Bioinformatics* 21:3852-3858, 2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is disclosed in U.S. Pat. Nos. 6,799,122; 6,913,879; and 6,996,476.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, a locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays.

V. Additional Breeding Techniques

A maize plant or seed provided herein can also be subject to additional breeding using one or more known methods in the art, e.g., pedigree breeding, recurrent selection, mass selection, and mutation breeding. Pedigree breeding starts with the crossing of two genotypes, such as a maize variety comprising an *Exserohilum turcicum* resistance gene or *Exserohilum turcicum* resistance allele or two coupled *Exserohilum turcicum* resistance QTLs or two coupled *Exserohilum turcicum* resistance alleles provided herein and another maize variety lacking such a locus. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-fertilization and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$, etc. After a sufficient amount of inbreeding, successive filial generations will serve to increase seed of the developed variety. The developed variety can comprise homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, a maize variety can be crossed with another variety to produce a first generation progeny plant. The first generation progeny plant can then be backcrossed to one of its parent varieties to create a $BC_1$ or $BC_2$. Progenies are selfed and selected so that the newly developed variety has many of the attributes of the recurrent parent and yet several of the desired attributes of the non-recurrent parent. This approach leverages the value and strengths of the recurrent parent for use in new maize varieties.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic line. A synthetic line is the resultant progeny formed by the intercrossing of several selected varieties.

Mass selection is another useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self-pollination, directed pollination could be used as part of the breeding program.

Mutation breeding can also be used to introduce new traits into a corn plant or seed provided herein. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, gamma rays (e.g., cobalt-60 or cesium-137), neutrons (product of nuclear fission by uranium-235 in an atomic reactor), beta radiation (emitted from radioisotopes such as phosphorus-32 or carbon-14), or ultraviolet radiation (from 2500 to 2900 nm)), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines). Transposon- or T-DNA-based mutagenesis is also encompassed by the present disclosure. Once a desired trait is observed through mutagenesis the trait can then be incorporated into existing germplasm by traditional breeding techniques.

VI. Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, "Northern Leaf Blight" or "NLB", or "Northern Corn Leaf Blight" or "NCLB", refers to a plant disease caused by the fungal pathogen *Exserohilum turcicum*, which is also known as *Helminthosporium turcicum* and *Setosphaeria turcica*.

As used herein, the term "cis configuration" or "cis linkage" refers to an arrangement in which two or more alleles are linked on the same parental chromosome. The term "trans configuration" or "trans linkage" refers to a configuration in which two or more alleles are arranged on different parental chromosomes.

As used herein, the terms "recombinant" or "recombined" in the context of a chromosomal segment refer to recombinant DNA sequences comprising one or more genetic loci in a configuration in which they are not found in nature, for example as a result of a recombination event between homologous chromosomes during meiosis.

As used herein, the term "plant" includes plant cells, plant protoplasts, plant cells of tissue culture from which sweet corn plants can be regenerated, plant calli, plant clumps and plant cells that are intact in plants or parts of plants such as pollen, flowers, seeds, leaves, stems, and the like.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "quantitative trait locus" (QTL) is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, "elite" or "cultivated" variety means any variety that has resulted from breeding and selection for superior agronomic performance, and therefore appropriate for commercial cultivation in the case of a hybrid variety, or for crossing to produce a hybrid variety that is cultivated. The term "cultivated" in reference to a plant or variety includes the parent lines of a hybrid cultivated corn variety. An "elite plant" refers to a plant belonging to an elite variety. Numerous elite varieties are available and known to those of skill in the art of corn breeding. An "elite population" is an assortment of elite individuals or varieties that can be used to represent the state of the art in terms of agronomically superior genotypes of a given crop species, such as corn. Similarly, an "elite germplasm" or elite strain of germplasm is an agronomically superior germplasm.

As used herein, "agronomically elite dent corn" in reference to a plant or variety refers to a plant or variety in which at least 95% of the genome originates from a dent corn variety that is elite as described herein above.

As used herein, the term "introgressed," when used in reference to a genetic locus, refers to a genetic locus that has been introduced into a new genetic background, such as through backcrossing. Introgression of a genetic locus can be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the terms "recombinant" or "recombined" in the context of a chromosomal segment refer to recombinant DNA sequences comprising one or more genetic loci in a configuration in which they are not found in nature, for example as a result of a recombination event between homologous chromosomes during meiosis.

As used herein, the term "linked," when used in the context of nucleic acid markers and/or genomic regions, means that the markers and/or genomic regions are located on the same linkage group or chromosome such that they tend to segregate together at meiosis.

As used herein, "tolerance locus" means a locus associated with tolerance or resistance to disease. For instance, a tolerance locus according to the present invention may, in one embodiment, control tolerance or susceptibility to *Exserohilum turcicum*.

As used herein, "tolerance" or "improved tolerance" in a plant refers to the ability of the plant to perform well, for example by maintaining yield, under disease conditions. Tolerance may also refer to the ability of a plant to maintain a plant vigor phenotype under disease conditions. Tolerance is a relative term, indicating that a "tolerant" plant is more able to maintain performance compared to a different (less tolerant) plant (e.g. a different plant variety) grown in similar disease conditions. One of skill will appreciate that plant tolerance to disease conditions varies widely, and can represent a spectrum of more-tolerant or less-tolerant phenotypes. However, by simple observation, one of skill can generally determine the relative tolerance of different plants, plant varieties, or plant families under disease conditions, and furthermore, will also recognize the phenotypic gradations of "tolerance."

As used herein "resistance" or "improved resistance" in a plant to disease conditions is an indication that the plant is more able to reduce disease burden than a non-resistant or less resistant plant. Resistance is a relative term, indicating that a "resistant" plant is more able to reduce disease burden compared to a different (less resistant) plant (e.g., a different plant variety) grown in similar disease conditions. One of skill will appreciate that plant resistance to disease conditions varies widely, and can represent a spectrum of more-resistant or less-resistant phenotypes. However, by simple observation, one of skill can generally determine the relative resistance of different plants, plant varieties, or plant families under disease conditions, and furthermore, will also recognize the phenotypic gradations of "resistant."

As used herein, "resistance allele" means the nucleic acid sequence associated with tolerance or resistance to disease.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

VII. Deposit Information

A deposit was made of at least 625 seeds of a sweet corn line, which comprises an introgression from Zea mays var. indentata, as described herein. The deposit was made with the American Type Culture Collection (ATCC), 10801 University Boulevard, Manassas, Va. 20110-2209 USA. The deposit is assigned ATCC Accession No. PTA-125393, and the date of deposit was Oct. 9, 2018. Access to the deposit will be available during the pendency of the application to persons entitled thereto upon request. The deposit has been accepted under the Budapest Treaty and will be maintained in the ATCC Depository, which is a public depository, for a period of 30 years, or 5 years after the most recent request, or for the enforceable life of the patent, whichever is longer, and will be replaced if nonviable during that period. Applicant does not waive any infringement of their rights granted under this patent or any other form of variety protection, including the Plant Variety Protection Act (7 U.S.C. 2321 et seq.).

EXAMPLES

Example 1. Identification of a Source with Broad-Spectrum Resistance to *Exserohilum turcicum*

Resistance to Northern Leaf Blight (NLB) in maize caused by *Exserohilum turcicum*, which is also known as *Setosphaeria turcica*, is conferred by both qualitative (monogenic) resistance and quantitative (polygenic) resistance. Qualitative genes for resistance to *Exserohilum turcicum* in maize that have been well characterized are Ht1, Ht2, Ht3, HtN, and HtM. There are known isolates of *Exserohilum turcicum* that can overcome each of these qualitative resistance genes. The isolates are characterized into races based on the resistance genes that they can overcome. Thus, races of *Exserohilum turcicum* are characterized as race 0, race 1, race 2, race 3, race N, race M, and all possible permutations thereof (e.g. race 12, race 2N, etc.), where the race number or letter indicates the Ht gene on which the isolate is virulent. Through multiple greenhouse assays, H111, was identified as providing resistance to all races of *Exserohilum turcicum*. H111 presents a resistant lesion type (small necrotic flecks) when inoculated with *Exserohilum turcicum* that can be distinguished from resistant lesion types resulting from other known resistance genes. H111 was derived from the cross B37×PI 209135. PI 209135, also known as Mayorbela, is a non-elite tropical population that has been well-characterized for its resistance to *Exserohilum turcicum*, and a number of other diseases including southern leaf blight, anthracnose, maize dwarf mosaic virus, and maize chlorotic dwarf virus. H111 was previously shown to be resistant to *Exserohilum turcicum* races 1 and 2. The gene HtM was reported to be present in the PI 209135-derived line H102 (C123×PI 209135), but this gene does not confer broad-spectrum resistance to *Exserohilum turcicum* isolates. Thus, H111 provides a novel source of resistance to *Exserohilum turcicum*.

Example 2. QTL Mapping of H111-Derived *Exserohilum turcicum* Resistance $F_2$-derived $F_3$ (F2:3) families from two bi-parental populations were developed to map loci conferring resistance to *Exserohilum turcicum* in line H111: "Inbred1"×H111 and "Inbred2"×H111. "Inbred1" and "Inbred2" are elite sweet corn inbred lines that are fully susceptible to *Exserohilum turcicum*. Both populations were evaluated in a replicated field trial when inoculated with a *Exserohilum turcicum* race 2NM isolate. Parametric linkage analysis identified a single QTL, spanning approximately 12 cM, on chromosome 8. This locus explained up to 97% of the observed phenotypic variance. This shows that the *Exserohilum turcicum* resistance from H111 is conferred by a single qualitative resistance gene. The effect of alleles at the QTL is primarily additive. The position of the QTL co-localizes with the known *Exserohilum turcicum* resistance gene cluster on chromosome 8 that also harbors the qualitative resistance genes Ht2 and HtN. Given that the populations were inoculated with a *Exserohilum turcicum* race 2NM isolate, which is virulent against Ht2, HtN, and HtM, the qualitative resistance from H111 is not conferred by Ht2, HtN, and/or HtM. Furthermore, HtM was reported to segregate independently of Ht2 and HtN, providing further support that the resistance demonstrated by line H111 was not due to the HtM gene identified from line H102. The resistance gene from H111 is novel and was designated as HtX.

From the two mapping populations, selected $F_3$ families derived from $F_2$ plants that were homozygous (resistant), susceptible or heterozygous for HtX were inoculated in the greenhouse with a *Exserohilum turcicum* race 2NM and a *Exserohilum turcicum* race 12 isolate. The presence of the HtX resistance gene explained 77-80% of the disease incidence (% of plants showing disease symptoms) in the F2:3 families against both isolates. For disease incidence in the greenhouse assay, the HtX gene acted in a dominant manner against *Exserohilum turcicum* race 2NM, while it acted in a partially dominant manner against *Exserohilum turcicum* race 12. A trait-linked marker, M1 (SEQ ID NO: 1), for detecting the presence of HtX was developed using a panel of 204 sweet corn inbred lines and has a genetic accuracy of 99.5%. M1 comprises a [C/T] change at 157,566,509 bp on chromosome 8 of the public maize B73 reference genome version 4.0 (B73 RefGen_v4) and can be used to track the trait in germplasm and distinguish it from the resistance conferred by Ht2 and HtN in the same genomic region.

Example 3. Efficacy of HtX to Confer Broad-Spectrum Resistance

Figure 3:
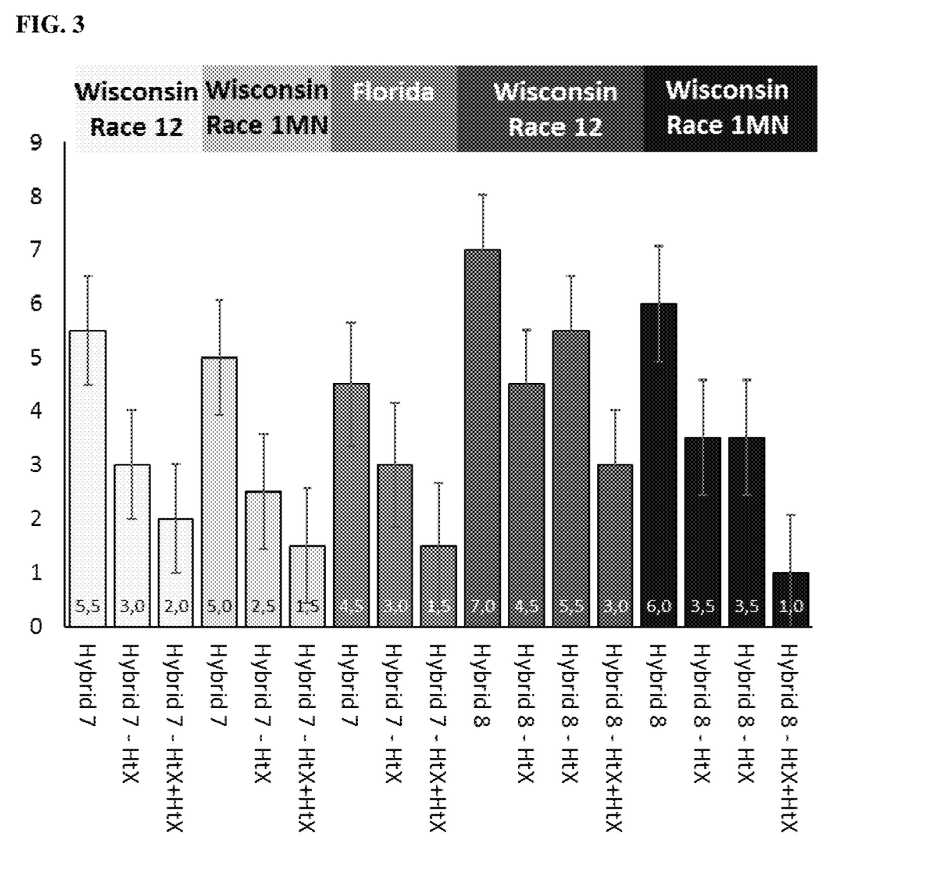
FIG. 3: Shows the average disease index (on a scale of 1-9) for two genetic backgrounds ("Hybrid 7" and "Hybrid 8") with differential deployment of the HtX gene tested at two locations in 2018. At the Wisconsin location, hybrids were inoculated with a specific *Exserohilum turcicum* race. At the Florida location, the hybrids' performance against natural infection was tested.

The resistance gene HtX was introduced into two different genetic backgrounds to test efficacy against a diverse panel of races in different locations in 2018. The co-dominant nature of the HtX gene was confirmed. The disease index was determined for all plants using a 1 to 9 scale. A rating of 1 is given to plants with little to no infection, defined as plants having at most a few scattered lesions in the lower regions of the plant; a rating of 3 is given to plants with light infection, which is defined as a moderate number of lesions on the lower leaves; a rating of 5 is given for moderate infection, which is defined as abundant lesions on lower leaves and few lesions on middle leaves; a rating of 7 is given to plants with heavy infection, which is defined as abundant lesions on lower and middle leaves and lesions extending to upper leaves; a rating of 9 is given to plants with very heavy infection, which is defined as plants having abundant lesions on all leaves and plants may have died prematurely. It was found that heterozygous deployment of HtX results lowers the disease index on a 1 to 9 scale by 2 points, while homozygous deployment lowers the disease index by an additional 2 points on average (FIG. 3). Therefore, a plant heterozygous for HtX shows intermediate to high resistance, characterized by mild symptoms, while a plant with homozygous HtX shows high resistance, with zero to negligible disease symptoms. A disease index <4 is considered commercially acceptable in temperate regions.

Figure 4:
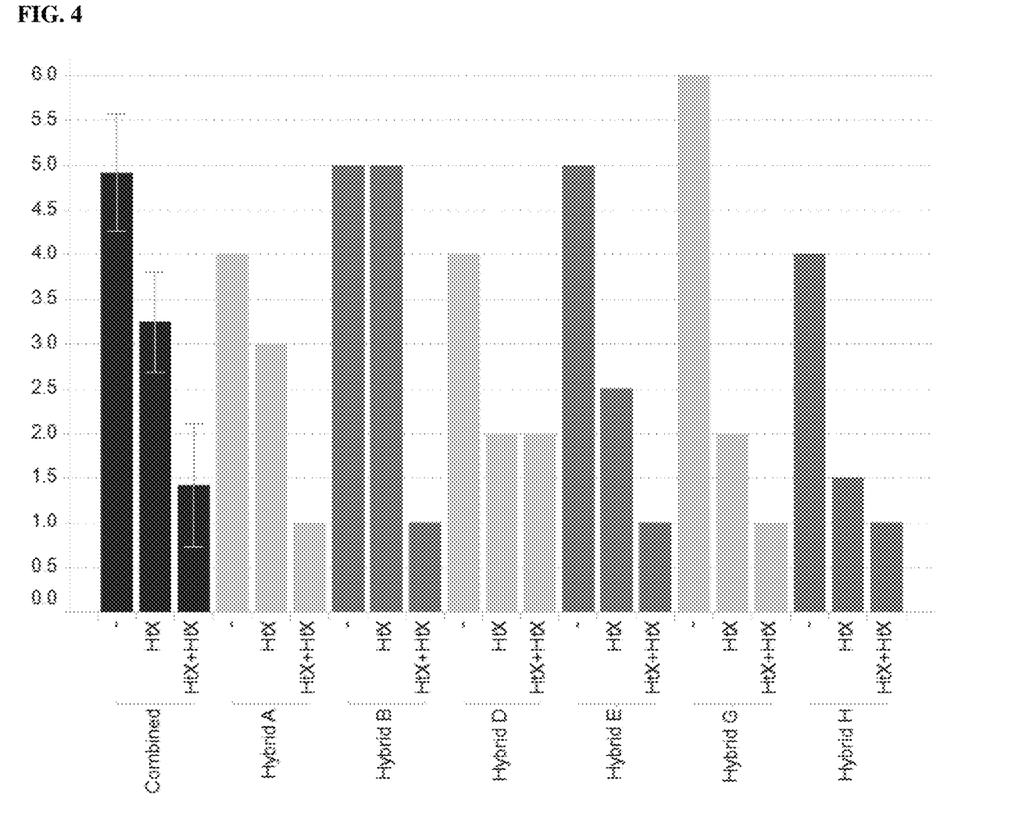
FIG. 4: Shows the average disease index (on a scale of 1-9) for six genetic backgrounds ("Hybrid A," "Hybrid B," "Hybrid D," "Hybrid E," "Hybrid G," and "Hybrid H") with differential deployment of the HtX gene tested in Florida in 2019. The hybrids' performance against natural infection was tested.

The HtX gene was introgressed in different configurations into six additional hybrid backgrounds in 2019. These hybrids (6 hybrid backgrounds×3 versions of each hybrid) were tested against natural infection from *Exserohilum turcicum* in Florida. The six hybrid backgrounds used in this trial were distinct from the two hybrid backgrounds tested in 2018. Each hybrid was tested in a single replication, but results were combined across hybrids for statistical analysis of the difference between the gene configurations. Plants heterozygous for HtX showed intermediate to high resistance, characterized by mild symptoms, while plants with homozygous HtX show high resistance, with zero to negligible disease symptoms, regardless of genetic background (FIG. 4). Furthermore, checks indicated that the races of *Exserohilum turcicum* in the field were virulent on all known resistance genes other than HtX. The results confirm the novel broad-spectrum resistance provided by the HtX gene and the additive mode of gene action across diverse genetic backgrounds.

The resistance conferred by the HtX gene may be stacked with the resistance traits conferred by other Ht genes. The HtX gene may be introduced into a maize plant that comprises a recombinant chromosomal segment comprising Ht2 and HtN resistance alleles in a cis configuration on chromosome 8. A coupling event between Ht2 and HtN can be created by crossing inbred lines B68HTN (carrying the HtN gene) and A619HT2 (carrying the Ht2 gene) and selecting for the recombination event between Ht2 and HtN. B68HTN and A619HT2 are both available from the U.S. National Plant Germplasm System. Table 1 shows markers associated with the Ht2 and HtX resistance alleles and can be used for selection of the recombination event. The trait-linked markers Q-NZMAY009401770 (SEQ ID NO: 2) and Q-ZMHt2 (SEQ ID NO: 3) are associated with Ht2 resistance alleles. The trait-linked markers Q-NZMAY009238970 (SEQ ID NO: 4) and Q-NZMAY009430172 (SEQ ID NO: 5) are associated with HtN resistance alleles.

The identification of a recombinant chromosomal segment comprising Ht2 and HtN resistance alleles in a cis configuration on chromosome 8 and markers associated with the recombination event is described in U.S. patent application Ser. No. 16/145,987, filed Sep. 28, 2018, the disclosure of which is incorporated herein by reference in its entirety.

TABLE 1

Trait-linked markers for Ht2 and HtN

| Marker | Marker Sequence (SEQ ID NO) | Physical Position | Favorable allele | Trait Linkage |
|---|---|---|---|---|
| Q-NZMAY009401770 | 2 | 152,245,739 | C | Ht2 |
| Q-ZMHt2 | 3 | 152,245,836 | T | Ht2 |
| Q-NZMAY009238970 | 4 | 152,358,289 | C | HtN |
| Q-NZMAY009430172 | 5 | 152,379,449 | C | HtN |

Example 4. Parentage of H111

As discussed above, H111 was derived from the cross B37×PI 209135. Inheritance of parental haplotypes in H111 was estimated by assaying 35,971 SNPs across the genome for both the parental source contributions. Genomic regions with high genotype similarity (>0.975) between B37 and H111 were assumed to indicate inheritance of the B37 haplotype by H111. Parental recombination breakpoints and haplotype blocks could be unambiguously defined using this method. Based on this analysis, the regions of the chromosomes of H111 derived from the parental haplotype of PI 209135 were identified. The location of the HtX gene was found on chromosome 8 within a chromosome segment inherited from PI 209135, confirming the origin of HtX from PI 209135 selection Mb.2. Overall, H111 was found to be 50% B37 in origin and 50% PI209135 selection Mb.2, which was considerably less B37 percentage than expected.

What is claimed is:

1. A sweet corn plant comprising an introgression from *Zea mays* var. *indentata* on chromosome 8, wherein said introgression comprises an allele from *Zea mays* var. *indentata* at marker M1 (SEQ ID NO: 1) in said plant, and wherein said introgression comprises a single gene conferring broad-spectrum resistance to *Exserohilum turcicum* relative to a plant lacking said introgression.

2. The plant of claim 1, wherein:
   a) said resistance to *Exserohilum turcicum* is additive;
   b) said introgression is about 12 cM or less;
   c) said broad-spectrum resistance comprises resistance to a plurality of *Exserohilum turcicum* races;
   d) the plant is homozygous for said introgression;
   e) a sample of seed comprising said introgression was deposited under ATCC Accession Number PTA-125393;
   f) said plant further comprises a recombinant chromosomal segment that comprises a first allele comprising an Ht2 locus and a second allele comprising an HtN locus, wherein said first allele and said second allele are configured in cis linkage on chromosome 8, and wherein said recombinant chromosomal segment confers resistance to *Exserohilum turcicum*; or
   g) the plant is further defined as an inbred or hybrid plant.

3. The plant of claim 2, wherein said broad-spectrum resistance comprises resistance to *Exserohilum turcicum* races 1, 2, M, and N.

4. A plant part of the plant of claim 1, wherein said plant part comprises the introgression.

5. The plant part of claim 4, wherein the plant part is a cell, a seed, a root, a stem, a leaf, an ear, a flower, or pollen.

6. A method for producing the plant of claim 1 with improved resistance to *Exserohilum turcicum*, comprising introgressing into said plant a chromosomal segment comprising an allele from *Zea mays* var. *indentata* on chromosome 8 that confers broad-spectrum resistance to *Exserohilum turcicum* relative to a plant lacking said allele, and wherein said resistance is additive.

7. The method of claim 6, wherein:
   a) said introgressing comprises:
      i) crossing a plant comprising said chromosomal segment with itself or with a second sweet corn plant of a different genotype to produce one or more progeny plants; and
      ii) selecting a progeny plant comprising said chromosomal segment;
   b) said broad-spectrum resistance comprises resistance to a plurality of *Exserohilum turcicum* races;
   c) a sample of seed comprising said chromosomal segment was deposited under ATCC Accession Number PTA-125393;
   d) said introgressing comprises backcrossing;
   e) said introgressing comprises marker-assisted selection; or
   f) said introgressing comprises assaying for said broad-spectrum resistance to *Exserohilum turcicum*.

8. The method of claim 7, wherein a) selecting a progeny plant comprises detecting a nucleic acid comprising marker locus M1 (SEQ ID NO: 1); b) the progeny plant is an $F_2$-$F_6$ progeny plant; or c) producing the progeny plant comprises backcrossing.

9. The method of claim 7, wherein said broad-spectrum resistance comprises resistance to *Exserohilum turcicum* races 1, 2, M, and N.

10. A plant produced by the method of claim 6.

11. A method for selecting a sweet corn plant with improved resistance to *Exserohilum turcicum*, comprising:
   a) crossing the plant of claim 1 with itself or with a second sweet corn plant of a different genotype to produce one or more progeny plants; and
   b) selecting a progeny plant comprising said introgression.

12. The method of claim 11, wherein:
   a) selecting said progeny plant comprises detecting a marker locus genetically linked to said introgression;
   b) selecting said progeny plant comprises detecting a nucleic acid comprising marker locus M1 (SEQ ID NO: 1);
   c) said resistance comprises resistance to a plurality of *Exserohilum turcicum* races;
   d) said progeny plant is an $F_2$-$F_6$ progeny plant; or
   e) producing said progeny plant comprises backcrossing.

13. The method of claim 12, wherein said resistance comprises resistance to *Exserohilum turcicum* races 1, 2, M, and N.

14. The plant of claim 2, wherein said recombinant chromosomal segment is flanked by marker loci Q-NZ-MAY009401770 (SEQ ID NO: 2) and Q-NZ-MAY009430172 (SEQ ID NO: 5) on chromosome 8.

15. The plant of claim 14, wherein said recombinant chromosomal segment is flanked by marker loci Q-ZMHt2 (SEQ ID NO: 3) and Q-NZMAY009238970 (SEQ ID NO: 4) on chromosome 8.

16. An agronomically elite dent corn plant comprising an introgression from *Zea mays* var. *indentata* on chromosome 8, wherein said introgression comprises an allele from *Zea mays* var. *indentata* at marker M1 (SEQ ID NO: 1) in said plant, and wherein said introgression comprises a single gene conferring broad-spectrum resistance to *Exserohilum turcicum* relative to a plant lacking said introgression.

17. The plant of claim 16, wherein:
   a) said broad-spectrum resistance comprises resistance to a plurality of *Exserohilum turcicum* races;
   b)) the plant is homozygous for said introgression; or
   c)) a sample of seed comprising said introgression was deposited under ATCC Accession Number PTA-125393.

18. A method for producing a plant of an elite corn variety with improved resistance to *Exserohilum turcicum*, comprising introgres sing into an elite corn variety an allele from *Zea mays* var. *indentata* comprising marker locus M1 (SEQ ID NO: 1) on chromosome 8 that confers broad-spectrum resistance to *Exserohilum turcicum* relative to a plant lacking said allele, and wherein said resistance is additive.

19. The method of claim 18, wherein:
   a) said introgressing comprises:
      i) crossing a plant comprising said chromosomal segment with itself or with a second corn plant of a different genotype to produce one or more progeny plants; and
      ii) selecting a progeny plant comprising said chromosomal segment;
   b) selecting a progeny plant comprises detecting a nucleic acid comprising marker locus M1 (SEQ ID NO: 1);
   c) the elite corn variety is a dent, flint or sweet corn variety; or
   d) the progeny plant is an $F_2$-$F_6$ progeny plant.

20. A plant produced by the method of claim 18.

* * * * *

UNITED STATES PATENT AND TRADEMARK OFFICE
CERTIFICATE OF CORRECTION

| | |
|---|---|
| PATENT NO. | : 11,382,291 B2 |
| APPLICATION NO. | : 16/721159 |
| DATED | : July 12, 2022 |
| INVENTOR(S) | : Eckard et al. |

It is certified that error appears in the above-identified patent and that said Letters Patent is hereby corrected as shown below:

In the Claims

In Column 25, Line 13, Claim 18, delete "introgres sing into an elite corn variety an allele from" and insert --introgressing into an elite corn variety an allele from--

Signed and Sealed this
Twenty-eighth Day of November, 2023

Katherine Kelly Vidal
*Director of the United States Patent and Trademark Office*

SEQUENCE LISTING

```
<160> NUMBER OF SEQ ID NOS: 5

<210> SEQ ID NO 1
<211> LENGTH: 252
<212> TYPE: DNA
<213> ORGANISM: Zea mays
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (145)..(145)
<223> OTHER INFORMATION: n is a, c, g, or t
```

<400> SEQUENCE: 1

```
atggtagaag tcctaataac aaggacagaa gaggttcttc tgaccggagg ggnagaaact    60
ctcgtgagcg cgccgacaga agctcctgtg agcgcgctga cagaagctct cgtgaacgcg   120
ccgayagaag gtgctcaatg gagcncaaag acatcaatta tgcatggaa tccagtgctt    180
ctgatagaag ctcatctggg ccatcagaga agcagctgta tgacaaacaa gggaagggta   240
tattccatcc tg                                                       252
```

<210> SEQ ID NO 2
<211> LENGTH: 160
<212> TYPE: DNA
<213> ORGANISM: Zea mays
<220> FEATURE:
<221> NAME/KEY: misc_feature
<222> LOCATION: (83)..(83)
<223> OTHER INFORMATION: n is a, c, g, or t

<400> SEQUENCE: 2

```
actctctcag gcttagctcc tcgctgaaca tggcgtcggt gggcttcttc ccagtgacga    60
cttcgagaag catcaccccg tanctgaaaa cgtcgctctt ccttgacgct ttaccggttg   120
aagcgtactc tgtagtaatt aatgtcagtt cacggcgaag                         160
```

<210> SEQ ID NO 3
<211> LENGTH: 61
<212> TYPE: DNA
<213> ORGANISM: Zea mays

<400> SEQUENCE: 3

```
gaggagctaa gcctgagaga gtgggtcagg caggctattc catcaggact cgctcatgtc    60
g                                                                    61
```

<210> SEQ ID NO 4
<211> LENGTH: 154
<212> TYPE: DNA
<213> ORGANISM: Zea mays
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t

<400> SEQUENCE: 4

```
ggttgtttcc actaagagac agtactgata agctggtaag gttagcaaat gtaccaggga    60
tgcttccatt gatgctgttg ttacctgctt gnaaantttc taggagcgtg ctatggtttc   120
caattgaagt tggtagcatc cctgtgaact catt                               154
```

<210> SEQ ID NO 5
<211> LENGTH: 193
<212> TYPE: DNA
<213> ORGANISM: Zea mays
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (57)..(58)
<223> OTHER INFORMATION: n is a, c, g, or t
<220> FEATURE:
<221> NAME/KEY: misc_feature

```
<222> LOCATION: (110)..(110)
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t

<400> SEQUENCE: 5
gtttatctcc gccttaagag gtagntgttc tggtgctcgg ttgcgtagca gtaaagnnag       60
ttttcgtcgt gatgctgcta ttactgaacc gggaggtatg cgacttctan gagtagttgc      120
ttattagcct acagaaaata tagggatctg gagactggtt atgtttcatg gctgttcttc      180
tttcaccngt acc                                                         193
```